(12) United States Patent
Rani et al.

(10) Patent No.: US 12,257,032 B2
(45) Date of Patent: Mar. 25, 2025

(54) METHODS AND SYSTEMS FOR DETERMINING BREATHING RATE AND HEART RATE FROM CARDIOPULMONARY SIGNALS

(71) Applicant: Tata Consultancy Services Limited, Mumbai (IN)

(72) Inventors: Smriti Rani, Kolkata (IN); Anwesha Khasnobish, Kolkata (IN); Arindam Ray, Kolkata (IN); Tapas Chakravarty, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 562 days.

(21) Appl. No.: 17/135,556

(22) Filed: Dec. 28, 2020

(65) Prior Publication Data

US 2021/0298607 A1 Sep. 30, 2021

(30) Foreign Application Priority Data

Mar. 28, 2020 (IN) .............................. 202021013673

(51) Int. Cl.
*A61B 5/0205* (2006.01)
*A61B 5/024* (2006.01)
*A61B 5/08* (2006.01)

(52) U.S. Cl.
CPC ............ *A61B 5/0205* (2013.01); *A61B 5/024* (2013.01); *A61B 5/0816* (2013.01)

(58) Field of Classification Search
CPC ..... A61B 5/0205; A61B 5/024; A61B 5/0816; A61B 5/0507; A61B 5/113; A61B 5/7221

(Continued)

(56) References Cited

U.S. PATENT DOCUMENTS

2020/0367764 A1* 11/2020 Le Guillou .......... A61B 5/0205

FOREIGN PATENT DOCUMENTS

KR 20190110305 A 6/2020

OTHER PUBLICATIONS

Christina Orphanidou et al., "Signal-Quality Indices for the Electrocardiogram and Photoplethysmogram: Derivation and Applications to Wireless Monitoring", Journal of Biomedical and Health Informatics, vol. 19, Issue: 3, 2014, Publisher: IEEE, https://www.researchgate.net/publication/264395822_Signal-Quality_Indices_for_the_Electrocardiogram_and_Photoplethysmogram_Derivation_and_Applications_to_Wireless_Monitoring/link/55a4f2a508ae81aec91324a3/download.

(Continued)

*Primary Examiner* — Christine H Matthews
*Assistant Examiner* — Chanel J Jhin
(74) *Attorney, Agent, or Firm* — Finnegan, Henderson, Farabow, Garrett & Dunner, LLP

(57) ABSTRACT

The disclosure generally relates to determining a breathing rate and a heart rate from cardiopulmonary signal. Conventional systems use additional hardware to improve signal quality or different signal processing techniques to calculate the heart rate from the cardiopulmonary signal. However accurately determining the heart rate is always a continuous area of an improvement. The present methods and systems solve the problem of determining the heart rate accurately, from the cardiopulmonary signals, by determining the signal quality of the cardiopulmonary signal and the signal associated with the heart rate, comprised in the cardiopulmonary signal. A signal processing technique that best performs, out of a set of signal processing techniques is identified based on the signal quality to determine the heart rate. A long-term and an effective health monitoring of healthy as well as (Continued)

patient and infant subjects is achieved by the present disclosure.

13 Claims, 11 Drawing Sheets

(58) Field of Classification Search
USPC .......................................................... 600/484
See application file for complete search history.

(56) References Cited

OTHER PUBLICATIONS

Nicolò Gambarotta et al., "A review of methods for the signal quality assessment to improve reliability of heart rate and blood pressures derived parameters," Medicine, Computer Science—Medical & Biological Engineering & Computing, 2016, Publisher: Semantic Scholar, https://www.semanticscholar.org/paper/A-review-of-methods-for-the-signal-quality-to-of-Gambarotta-Aletti/175269094f565f701c2780b88190be775d4c1a7c.

Po Li et al., "Cancellation in Noncontact Microwave Doppler Radar Cardiopulmonary Sensing," International Journal of Digital Content Technology and its Applications, 2012, Publisher: Research Gate, https://www.researchgate.net/publication/272810720_Harmonics_Cancellation_in_Noncontact_MicrowaveDoppler_Radar_Cardiopulmonary_Sensing.

Sarah El-Samad et al. "Heartbeat rate measurement using microwave systems: single-antenna, two-antennas, and modeling a moving person," Title of the item: Analog Integrated Circuits and Signal Processing, 2018, Publisher: Research Gate, https://hal.archives-ouvertes.fr/hal-01769423/document.

* cited by examiner

METHODS AND SYSTEMS FOR DETERMINING BREATHING RATE AND HEART RATE FROM CARDIOPULMONARY SIGNALS

PRIORITY CLAIM

This U.S. patent application claims priority under 35 U.S.C. § 119 to: Indian Patent Application No. 202021013673, filed on 28 Mar. 2020. The entire contents of the aforementioned application are incorporated herein by reference.

TECHNICAL FIELD

The disclosure herein generally relates to monitoring cardiopulmonary signals, and, more particularly, to methods and systems for determining a breathing rate and a heart rate from cardiopulmonary signal based on signal quality.

BACKGROUND

Cardiopulmonary signals contain vital signs of a subject, including a breathing rate and a heart rate. Unobtrusive and continuous monitoring of the cardiopulmonary signals for determining the breathing rate and the heart rate, finds importance in long-term health monitoring of healthy as well as patient and infant subjects. The long-term health monitoring includes not only in medical care units and hospitals, but also in other areas such as fitness tracking, stress monitoring, presence detection in rescue operations and so on. There are many signal processing techniques present in the art to determine the breathing rate and the heart rate of the subject to be monitored, from the cardiopulmonary signals. However, determining the breathing rate and the heart rate accurately from the sensitive cardiopulmonary signal is challenging and is always a continuous area of an improvement.

SUMMARY

Embodiments of the present disclosure present technological improvements as solutions to one or more of the above-mentioned technical problems recognized by the inventors in conventional systems.

In an aspect, there is provided a processor-implemented method for determining a breathing rate and a heart rate from cardiopulmonary signals. The method comprising the steps of: receiving, via one or more hardware processors, a cardiopulmonary signal of a subject being monitored, from a sensor unit; splitting, via the one or more hardware processors, the cardiopulmonary signal into one or more sub-cardiopulmonary signals, based on a predefined cardiopulmonary signal window duration; pre-processing, via the one or more hardware processors, each sub-cardiopulmonary signal of the one or more sub-cardiopulmonary signals, to obtain a pre-processed sub-cardiopulmonary signal, for each sub-cardiopulmonary signal; filtering, by a bandpass filter implemented via the one or more hardware processors, the pre-processed sub-cardiopulmonary signal of each sub-cardiopulmonary signal, to obtain a first filtered signal and a second filtered signal, wherein the first filtered signal having frequencies between a predetermined first range of frequencies corresponding to breathing associated with the subject being monitored, and the second filtered signal having frequencies between a predetermined second range of frequencies corresponding to heartbeats associated with the subject being monitored; determining, via the one or more hardware processors, a breathing rate of the subject being monitored, from the first filtered signal, by using a spectrum analysis technique; post-processing, via the one or more hardware processors, the second filtered signal to obtain a post-processed signal, wherein the post-processing comprises removing low frequency components underlying in the second filtered signal; obtaining, via the one or more hardware processors, an overall signal quality value of each sub-cardiopulmonary signal, and a heart signal quality value of the second filtered signal corresponding to each sub-cardiopulmonary signal; and determining, via the one or more hardware processors, a heart rate of the subject being monitored, using one of a set of signal processing techniques on the post-processed signal, based on the overall signal quality value and the heart signal quality value, wherein the set of signal processing techniques comprises (i) a sliding window based additive spectra technique, (ii) a mean peak to peak time difference technique and (iii) a minimum variance sweep technique.

In another aspect, there is provided a system for determining a breathing rate and a heart rate from cardiopulmonary signals, the system comprising: a memory storing instructions; one or more Input/Output (I/O) interfaces; and one or more hardware processors coupled to the memory via the one or more I/O interfaces, wherein the one or more hardware processors are configured by the instructions to: receive a cardiopulmonary signal of a subject being monitored, from a sensor unit; split the cardiopulmonary signal into one or more sub-cardiopulmonary signals, based on a predefined cardiopulmonary signal window duration; pre-process each sub-cardiopulmonary signal of the one or more sub-cardiopulmonary signals, to obtain a pre-processed sub-cardiopulmonary signal, for each sub-cardiopulmonary signal; filter, the pre-processed sub-cardiopulmonary signal of each sub-cardiopulmonary signal, to obtain a first filtered signal and a second filtered signal, using a bandpass filter, wherein the first filtered signal having frequencies between a predetermined first range of frequencies corresponding to breathing associated with the subject being monitored, and the second filtered signal having frequencies between a predetermined second range of frequencies corresponding to heartbeats associated with the subject being monitored; determine a breathing rate of the subject being monitored, from the first filtered signal, by using a spectrum analysis technique; post-process the second filtered signal to obtain a post-processed signal, wherein the post-processing comprises removing low frequency components underlying in the second filtered signal; obtain an overall signal quality value from each sub-cardiopulmonary signal, and a heart signal quality value from the second filtered signal corresponding to each sub-cardiopulmonary signal; and determine a heart rate of the subject being monitored, using one of a set of signal processing techniques on the post-processed signal, based on the overall signal quality value and the heart signal quality value, wherein the set of signal processing techniques comprises (i) a sliding window based additive spectra technique, (ii) a mean peak to peak time difference technique and (iii) a minimum variance sweep technique.

In yet another aspect, there is provided a computer program product comprising a non-transitory computer readable medium having a computer readable program embodied therein, wherein the computer readable program, when executed on a computing device, causes the computing device to: receive a cardiopulmonary signal of a subject being monitored, from a sensor unit; split the cardiopulmonary signal into one or more sub-cardiopulmonary signals, based on a predefined cardiopulmonary signal window duration; pre-process each sub-cardiopulmonary signal of the one or more sub-cardiopulmonary signals, to obtain a pre-processed sub-cardiopulmonary signal, for each sub-cardiopulmonary signal; filter, the pre-processed sub-cardiopulmonary signal of each sub-cardiopulmonary signal, to obtain a first filtered signal and a second filtered signal, using a bandpass filter, wherein the first filtered signal having frequencies between a predetermined first range of frequencies corresponding to breathing associated with the subject being monitored, and the second filtered signal having frequencies between a predetermined second range of frequencies corresponding to heartbeats associated with the subject being monitored; determine a breathing rate of the subject being monitored, from the first filtered signal, by using a spectrum analysis technique; post-process the second filtered signal to obtain a post-processed signal, wherein the post-processing comprises removing low frequency components underlying in the second filtered signal; obtain an overall signal quality value from each sub-cardiopulmonary signal, and a heart signal quality value from the second filtered signal corresponding to each sub-cardiopulmonary signal; and determine a heart rate of the subject being monitored, using one of a set of signal processing techniques on the post-processed signal, based on the overall signal quality value and the heart signal quality value, wherein the set of signal processing techniques comprises (i) a sliding window based additive spectra technique, (ii) a mean peak to peak time difference technique and (iii) a minimum variance sweep technique.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
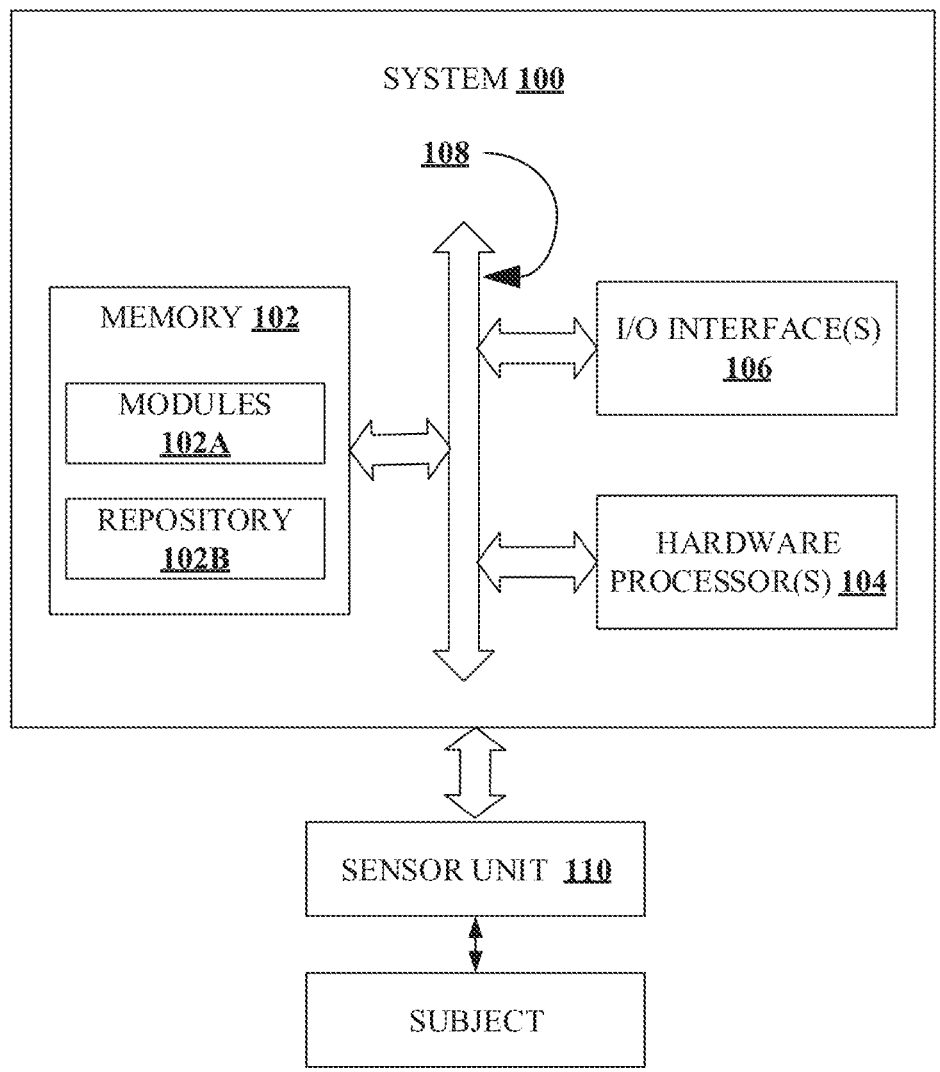
FIG. 1 is an exemplary block diagram of a system for determining a breathing rate and a heart rate from cardiopulmonary signal, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Cardiopulmonary signals carryout several hidden components related to vital signs including a breathing rate, a heart rate and other artifacts. Unobtrusive and continuous detection of the vital signs from the cardiopulmonary signals of a subject plays a vital role in monitoring health status of the subject. In the context of the present disclosure, the expression 'subject' refers to a living being such as a human being or an animal. Conventional systems use different kinds of sensing units to acquire the cardiopulmonary signals of the subject being monitored for checking the health status. However, due to various stationery objects and movements of the subject, it may be always a challenge to acquire a cardiopulmonary signal with good quality so that the vital signs such as the breathing rate and the heart rate may be accurately determined. State-of-the-art uses additional techniques or extra hardware (s) to improve the quality of the cardiopulmonary signals. However due to overlapping nature of the hidden components themselves in the cardiopulmonary signal, there may be a challenge to separate signals associated with the hidden components, specifically the signal related to the heart rate which is more sensitive than the other vital signs. Hence the quality of the signals after the separation may be affected.

Further, the state-of-the-art uses different signal processing techniques to determine the heart rate from the cardiopulmonary signal. The signal processing techniques include time-domain based signal processing techniques and frequency-domain based signal processing techniques. Different quality of the cardiopulmonary signals may give different heart rate readings with different available signal processing techniques. Hence to find a suitable signal processing technique out of the several signal processing techniques to determine the heart rate accurately, based on the signal quality of the cardiopulmonary signal, may always be a challenging task.

The present disclosure herein provide methods and systems for determining the breathing rate and the heart rate from cardiopulmonary signals, solves the problem of determining the heart rate accurately, from the cardiopulmonary signals. According to the present disclosure, the signal quality of the cardiopulmonary signal and the signal associated with the heart rate, comprised in the cardiopulmonary signal are determined. Then, one of the signal processing technique that best performs, out of a set of signal processing techniques is employed on the cardiopulmonary signal, based on the signal quality, to determine the heart rate.

Referring now to the drawings, and more particularly to FIG. 1 through FIG. 7B, where similar reference characters denote corresponding features consistently throughout the figures, there are shown preferred embodiments and these embodiments are described in the context of the following exemplary systems and/or methods.

FIG. 1 is an exemplary block diagram of a system 100 for determining the breathing rate and the heart rate from the cardiopulmonary signal, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface, and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computer, notebooks, hand-held devices, workstations, mainframe computers, servers, a network cloud and the like.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules 102A and a repository 102B for storing data processed, received, and generated by one or more of the plurality of modules 102A. The plurality of modules 102A may include routines, programs, objects, components, data structures, and so on, which perform particular tasks or implement particular abstract data types.

The plurality of modules 102A may include programs or computer-readable instructions or coded instructions that supplement applications or functions performed by the system 100. The plurality of modules 102A may also be used as, signal processor(s), state machine(s), logic circuitries, and/or any other device or component that manipulates signals based on operational instructions. Further, the plurality of modules 102A can be used by hardware, by computer-readable instructions executed by the one or more hardware processors 104, or by a combination thereof. In an embodiment, the plurality of modules 102A can include various sub-modules (not shown in FIG. 1). Further, the memory 102 may include information pertaining to input(s)/output(s) of each step performed by the processor(s) 104 of the system 100 and methods of the present disclosure.

The repository 102B may include a database or a data engine. Further, the repository 102B amongst other things, may serve as a database or includes a plurality of databases for storing the data that is processed, received, or generated as a result of the execution of the plurality of modules 102A. Although the repository 102B is shown internal to the system 100, it will be noted that, in alternate embodiments, the repository 102B can also be implemented external to the system 100, where the repository 102B may be stored within an external database (not shown in FIG. 1) communicatively coupled to the system 100. The data contained within such external database may be periodically updated. For example, new data may be added into the external database and/or existing data may be modified and/or non-useful data may be deleted from the external database. In one example, the data may be stored in an external system, such as a Lightweight Directory Access Protocol (LDAP) directory and a Relational Database Management System (RDBMS). In another embodiment, the data stored in the repository 102B may be distributed between the system 100 and the external database. The components and functionalities of the system 100 are described further in detail with reference to FIG. 2, FIG. 3A and FIG. 3B.

In an embodiment, the system 100 is connected to a sensor unit 110. The sensor unit 110 is configured to receive the cardiopulmonary signal from the subject being monitored. The sensor unit 110 may be one or in a combination of a sensor group that are capable of acquiring the cardiopulmonary signal from the subject being monitored. In an embodiment, the sensor group includes but are not limited to pneumotachograph, ultrasound sensors, accelerometers including wearable accelerometers, respiratory belts, and radars including single-channel radars and multi-channel radars. Furthermore, the radars including an indented radar disclosed in the Indian patent application numbered 201921043573 of the applicant. In an embodiment, the sensor unit 110 may be integral part of the system 100 or may be externally connected to the system 100 through the I/O interface(s) 106 either wireless or with a wired connection.

Figure 2:
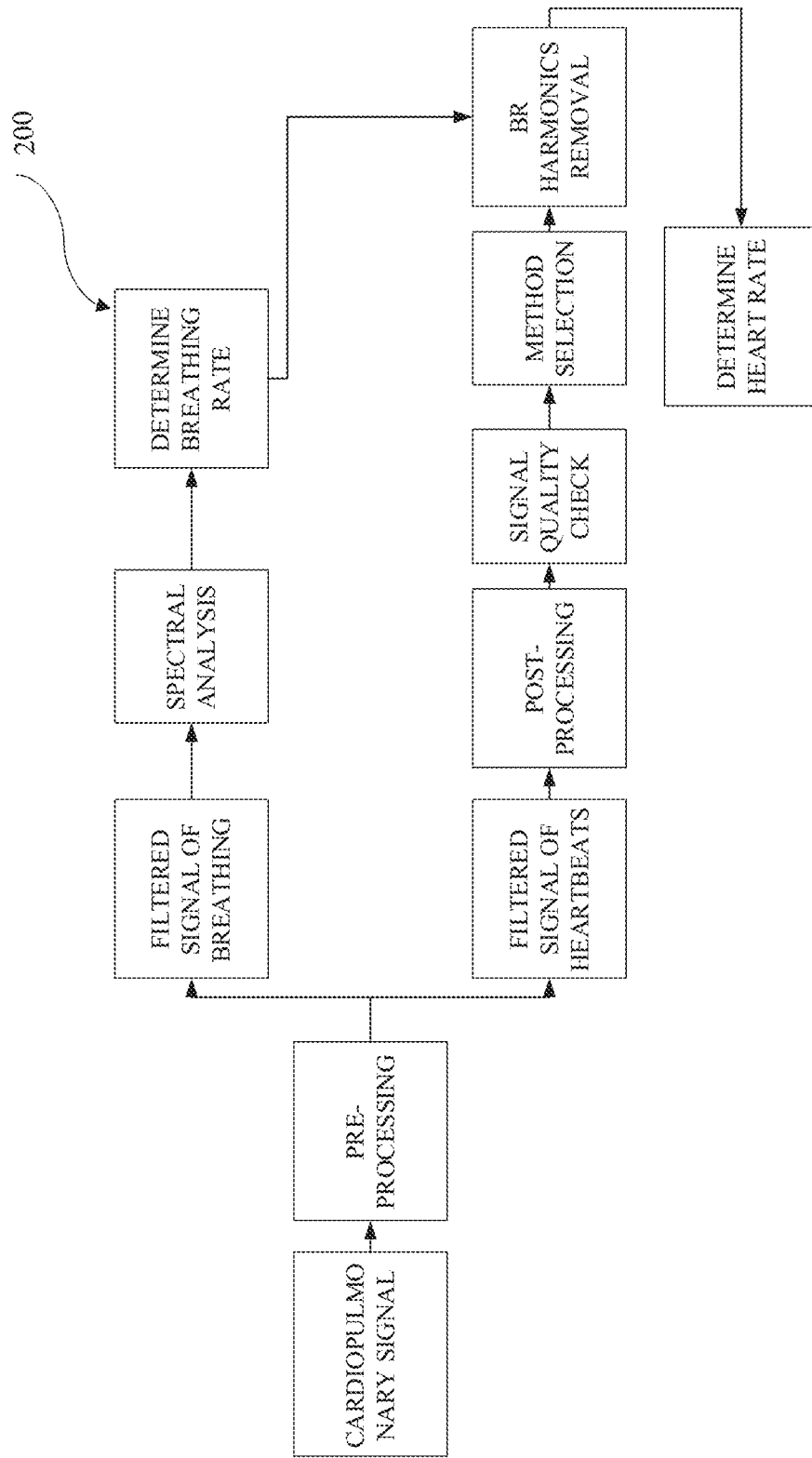
FIG. 2 illustrates a high-level flow chart of a processor-implemented method for determining the breathing rate and the heart rate from the cardiopulmonary signal, in accordance with some embodiments of the present disclosure.

FIG. 2 illustrates a high-level flow chart of a processor-implemented method for determining the breathing rate and the heart rate from the cardiopulmonary signal, in accordance with some embodiments of the present disclosure. The cardiopulmonary signal is analyzed to check the signal quality. A signal processing technique among the set of signal processing techniques is utilized based on the signal quality, to determine the heart rate of the subject accurately. The breathing rate of the subject is determined by performing a spectrum analysis on the cardiopulmonary signal.

Figure 3A:
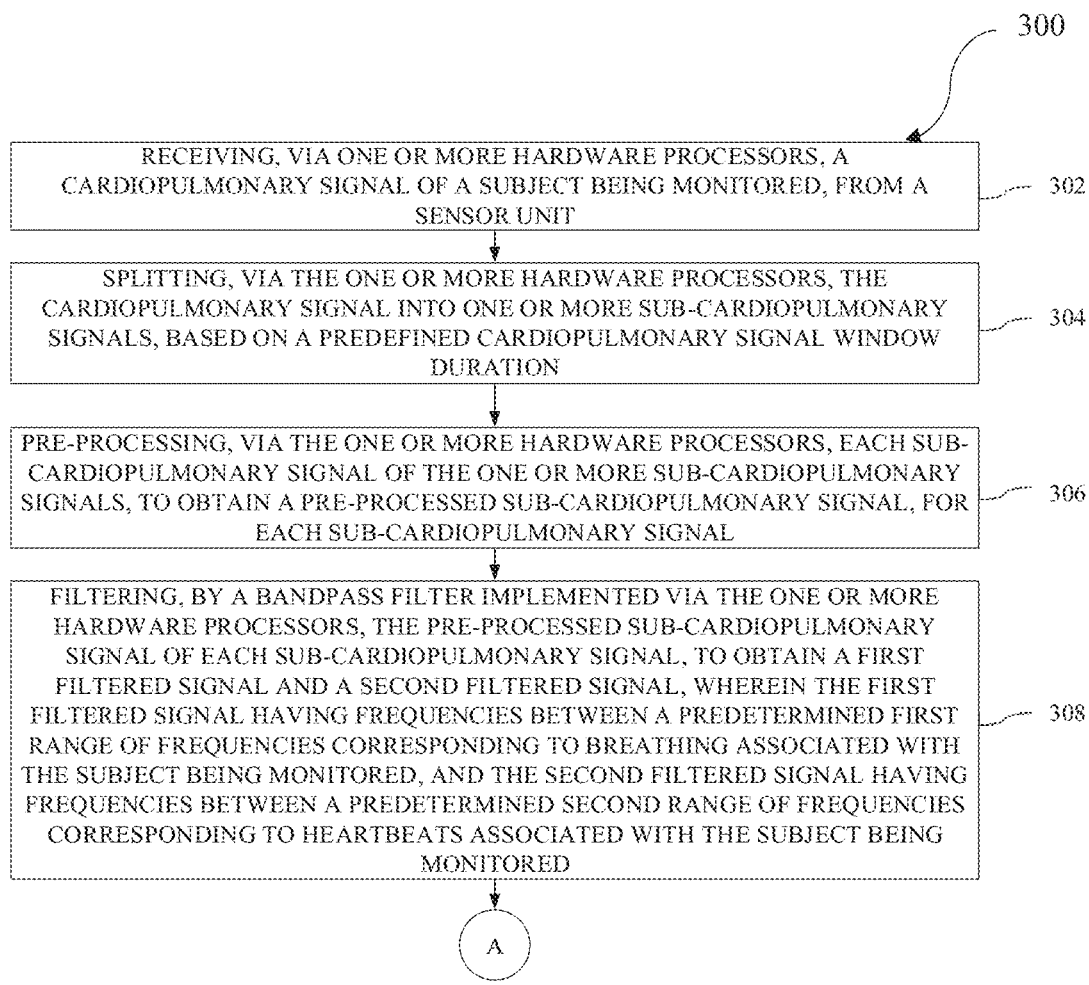
FIG. 3A and FIG. 3B illustrate exemplary flow diagrams of a processor-implemented method for determining the breathing rate and the heart rate from the cardiopulmonary signal, in accordance with some embodiments of the present disclosure.
Figure 3B:
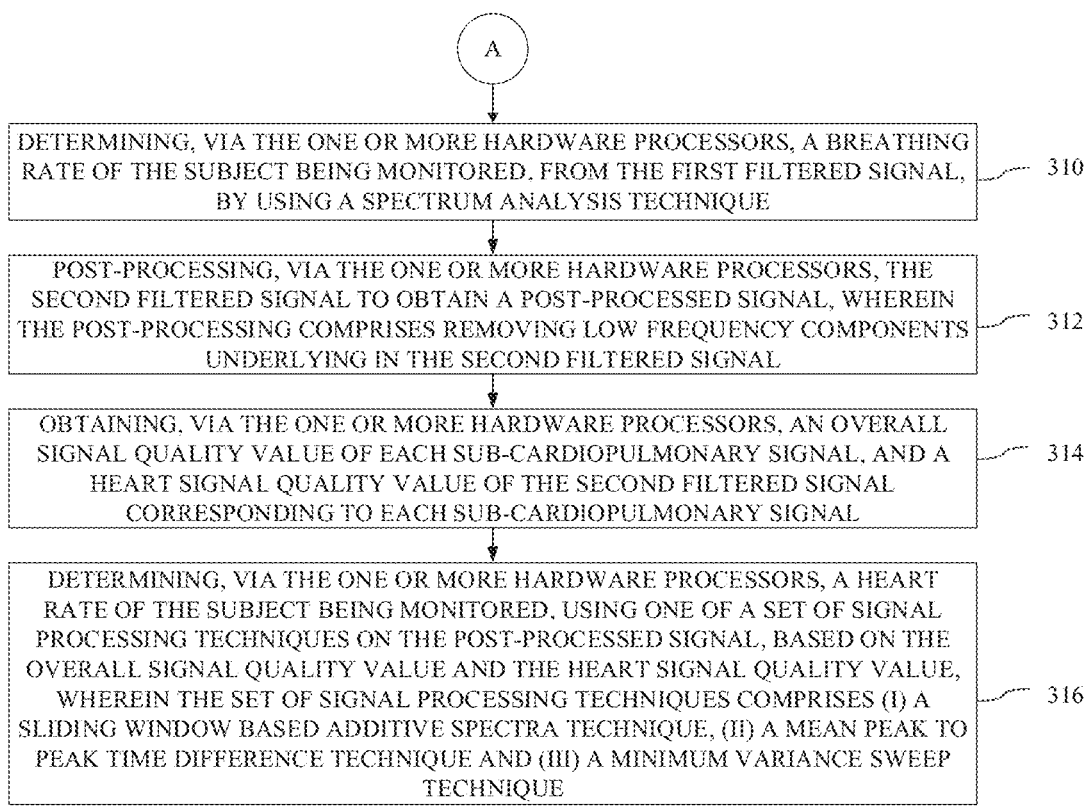

Referring to FIG. 3A and FIG. 3B, components and functionalities of the system 100, and the functionalities of the method 200 are described in accordance with an example embodiment of the present disclosure. FIG. 3A and FIG. 3B illustrate exemplary flow diagrams of a processor-implemented method for determining the breathing rate and the heart rate from the cardiopulmonary signal, in accordance with some embodiments of the present disclosure. Although steps of the method 300 including process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any practical order. Further, some steps may be performed simultaneously, or some steps may be performed alone or independently.

At step 302 of the method 300, the one or more hardware processors 104 of the system 100 are configured to receive the cardiopulmonary signal of the subject being monitored, from the sensor unit 110. The sensor unit 110 is configured to acquire the cardiopulmonary signal from the subject being monitored. In an embodiment, if the sensor unit 110 is within the system 100, then the system 100 is placed beside or near to the subject being monitored to acquire the cardiopulmonary signal. If the sensor unit 110 is connected to the system 100 but present outside, then the sensor unit 110 is placed beside or near to the subject (sometimes subject may wear the sensor unit 110) the being monitored to acquire the cardiopulmonary signal. In an embodiment, the cardiopulmonary signal is a continuous and an unobtrusive time-domain signal represented in seconds.

At step 304 of the method 300, the one or more hardware processors 104 of the system 100 are configured to split the cardiopulmonary signal into one or more sub-cardiopulmonary signals, based on a predefined cardiopulmonary signal window duration. Generally, a breath cycle of the subject may be of 3 to 4 seconds duration. If the cardiopulmonary signal window duration is less than 10 seconds, then it may be difficult to capture 2 to 3 breaths in a cycle. In accordance with the present disclosure, based on domain knowledge, the predefined cardiopulmonary signal window duration is at least 10 seconds or multiples of '5' but not '5' (for example, 10 seconds, 15 seconds, 20 seconds etc.). Each sub-cardiopulmonary signal of the one or more sub-cardiopulmonary signals is separately analyzed and monitored continuously, in the order in which it is received, for determining the heart rate and the breathing rate.

At step 306 of the method 300, the one or more hardware processors 104 of the system 100 are configured to pre-process each sub-cardiopulmonary signal of the one or more sub-cardiopulmonary signals, to obtain a pre-processed sub-cardiopulmonary signal, for each sub-cardiopulmonary signal. In an embodiment, each sub-cardiopulmonary signal of the one or more sub-cardiopulmonary signals is filtered using a bandpass filter to obtain a filtered sub-cardiopulmonary signal for each sub-cardiopulmonary signal. In an embodiment, the filtered sub-cardiopulmonary signal may be having frequencies between a predetermined third range of frequencies. The predetermined third range of frequencies corresponding to the breathing and the heartbeats associated with the subject being monitored. Generally, the range of frequencies associated with the breathing and the heartbeats at rest state is typically 0.2 Hz to 2 Hz, based on the domain knowledge. Hence the predetermined third range of frequencies may be for example, 0.2 Hz to 2 Hz. In another embodiment, the predetermined third range of frequencies may be for example, 0.2 Hz to 3 Hz in case the subject is performing a task such as running, fitness exercises and so on. Then, a mean removal and an amplitude normalization are performed on the filtered sub-cardiopulmonary signal to obtain the pre-processed sub-cardiopulmonary signal. A noise and the other unwanted artifacts present in the filtered sub-cardiopulmonary signal may be removed from the mean removal and the amplitude normalization.

In an embodiment, the bandpass filter may be a software filter or a hardware filter. If it is the software filter, then such filter may be present as one of the module of the plurality of modules 102A. If it is the hardware filter, then such filter may be integral part of the system 100, wherein the one or more hardware processors 104 may be configured to serve as the bandpass filter, or such filter may be external to the system 100, may be connected or communicated with the system 100 either wirelessly or with the wired connection, through the I/O interface(s) 106.

At step 308 of the method 300, the one or more hardware processors 104 of the system 100 are configured to filter the pre-processed sub-cardiopulmonary signal of each sub-cardiopulmonary signal obtained at step 304 of the method 300, using the bandpass filter to obtain a first filtered signal and a second filtered signal separately. In an embodiment, the first filtered signal having frequencies between a predetermined first range of frequencies corresponding to breathing associated with the subject being monitored. The predetermined first range of frequencies may be for example, 0.2 Hz to 0.8 Hz, which is identified as general breathing frequency range based on the domain knowledge. Similarly, the second filtered signal having frequencies between a predetermined second range of frequencies corresponding to the heartbeats associated with the subject being monitored. The predetermined second range of frequencies may be for example, 1 Hz to 2 Hz, which is identified as general heartbeats frequency range based on the domain knowledge.

At step 310 of the method 300, the one or more hardware processors 104 of the system 100 are configured to determine the breathing rate of the subject being monitored, from the first filtered signal, using a spectrum analysis technique. In an embodiment, according to the spectrum analysis technique, the first filtered signal is transformed to a frequency domain signal using a Fast Fourier Transform (FFT) technique. Then, the breathing rate of the subject being monitored is obtained in breaths per minute based on a frequency associated with a highest peak of the frequency domain signal. In the scenario where the subject is a human being, the breathing rate in breaths per minute is obtained based on the below relation:

$$\text{Breathing rate in breaths per minute} = F_{hp} * 60$$

where, $F_{hp}$ is the frequency associated with the highest peak of the frequency domain signal.

At step 312 of the method 300, the one or more hardware processors 104 of the system 100 are configured to post-process the second filtered signal associated with each sub-cardiopulmonary signal obtained at step 304 of the method 300, to obtain a post-processed signal. In an embodiment, low frequency components having slowly varying nature, that are underlying in the second filtered signal are removed to obtain the post-processed signal. In an embodiment, a tenth order polynomial is applied on the second filtered signal to identify the low frequency components and such identified low frequency components are removed from the second filtered signal to obtain the post-processed signal. The post-processed signal associated with each sub-cardiopulmonary signal obtained at step 304 of the method 300 is analyzed and further processed to obtain the heart rate of the subject being monitored.

At step 314 of the method 300, the one or more hardware processors 104 of the system 100 are configured to obtain an overall signal quality value and a heart signal quality value. In an embodiment, the overall signal quality value is obtained from each sub-cardiopulmonary signal obtained at step 304 of the method 300. The heart signal quality value is obtained from the second filtered signal corresponding to each sub-cardiopulmonary signal, obtained at step 308 of the method 300. The overall signal quality value and the heart signal quality value helps to assess the signal quality of the cardiopulmonary signal received at step 302 of the method 300 to determine the heart rate accurately.

In an embodiment, an overall signal autocorrelation curve whose envelope having a triangular contour, is generated by applying an autocorrelation function on the sub-cardiopulmonary signal. An area under the envelope of the overall signal autocorrelation curve may be defined as the overall signal quality value for the sub-cardiopulmonary signal. Similarly, a heart signal autocorrelation curve whose envelope having the triangular contour, is generated by applying the autocorrelation function on the second filtered signal corresponding to the sub-cardiopulmonary signal. An area under the envelope of the heart signal autocorrelation curve may be defined as the heart signal quality value for the second filtered signal corresponding to the sub-cardiopulmonary signal.

Figure 4:
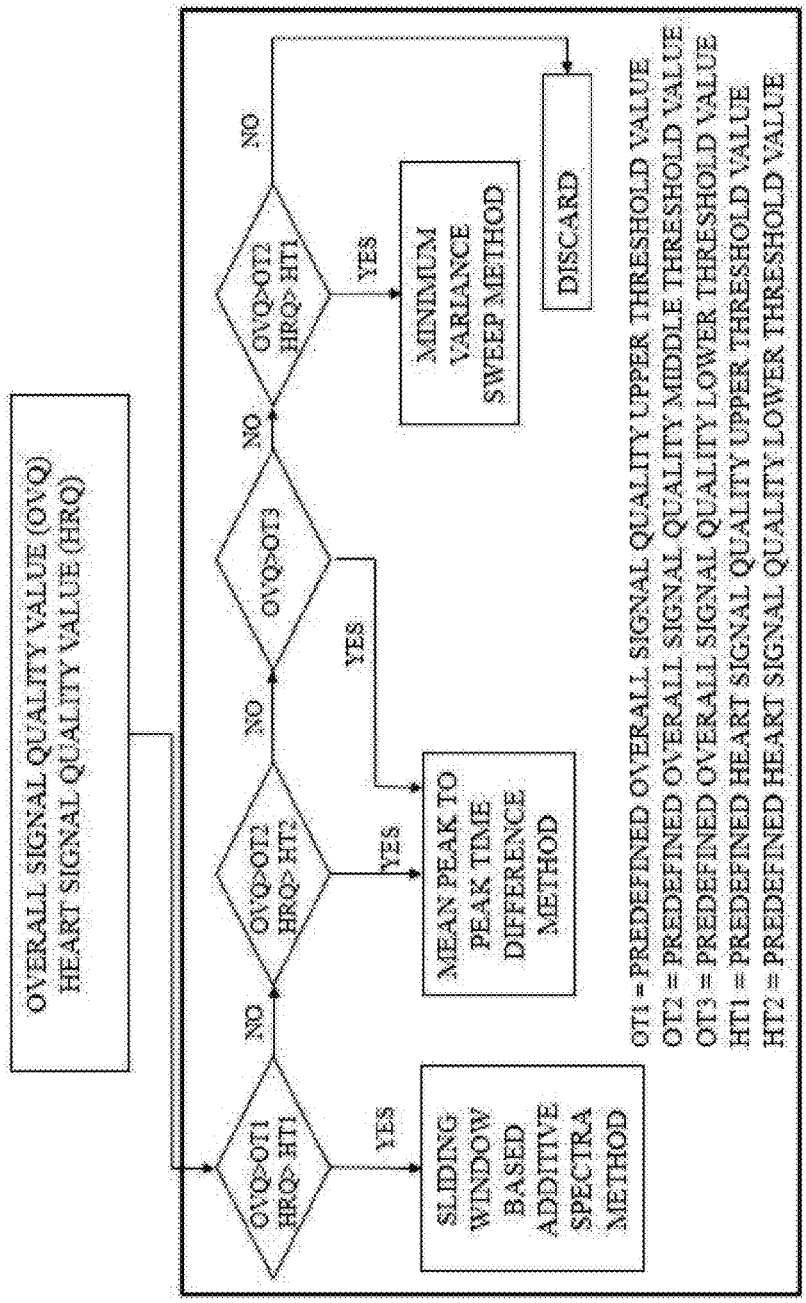
FIG. 4 is an exemplary flowchart showing a selection of a signal processing technique from a set of signal processing techniques based on signal quality, in accordance with some embodiments of the present disclosure.

At step 316 of the method 300, the one or more hardware processors 104 of the system 100 are configured to determine the heart rate of the subject being monitored, using one of a set of signal processing techniques on the post-processed signal obtained at step 312 of the method 300, based on the overall signal quality value obtained at step 314 of the method 300 and the heart signal quality value obtained at step 314 of the method 300. The set of signal processing techniques include: (i) sliding window based additive spectra technique, (ii) mean peak to peak time difference technique and (iii) minimum variance sweep technique. FIG. 4 is an exemplary flowchart showing a selection of the signal processing technique from the set of signal processing techniques based on the signal quality, in accordance with some embodiments of the present disclosure.

In an embodiment, the heart rate is determined from the post-processed signal, using the sliding window based additive spectra technique, when (i) the overall signal quality value is greater than a predefined overall signal quality upper threshold value, and (ii) the heart signal quality value is greater than a predefined heart signal quality upper threshold value. The overall signal quality value is greater than the predefined overall signal quality upper threshold value indicates that the signal quality of the sub-cardiopulmonary signal is good. Similarly, the heart signal quality value is greater than the predefined heart signal quality upper threshold value, indicates that the signal quality of the heartbeat signal (the second filtered signal obtained at step 308 of the method 300, associated with the sub-cardiopulmonary signal) is good. Hence the signal quality is good enough with useful information to determine the heart rate, the frequency domain sliding window based additive spectra technique is employed. In an embodiment, the predefined overall signal quality upper threshold value may be for example '4' and the predefined heart signal quality upper threshold value may be for example '2'.

In an embodiment, the heart rate is determined from the post-processed signal, using the mean peak to peak time difference technique, when (i) the overall signal quality value is greater than a predefined overall signal quality lower threshold value, or (ii) (a) the overall signal quality value is greater than a predefined overall signal quality middle threshold value and (b) the heart signal quality value is greater than a predefined heart signal quality lower threshold value. The above conditions indicate that a mediocre signal quality for both the sub-cardiopulmonary signal and the heartbeat signal (the second filtered signal obtained at step 308 of the method 300, associated with the sub-cardiopulmonary signal). Since some useful information related to heart rate may still present, a time domain based signal processing technique such as the mean peak to peak time difference technique may be employed to determine the heart rate. In an embodiment, the predefined overall signal quality middle threshold value may be for example '2.3', the predefined overall signal quality lower threshold value may be for example '1' and the predefined heart signal quality lower threshold value may be for example '1.1'.

In an embodiment, the heart rate is determined from the post-processed signal, using the minimum variance sweep technique, when (i) the overall signal quality value is greater than the predefined overall signal quality middle threshold value, and (ii) the heart signal quality value is greater than the predefined heart signal quality upper threshold value. The above conditions indicate that a low signal quality for both the sub-cardiopulmonary signal and the heartbeat signal (the second filtered signal obtained at step 308 of the method 300, associated with the sub-cardiopulmonary signal). Since some portions in the sub-cardiopulmonary signal may contain useful information related to heart rate, a time domain based signal processing technique such as the minimum variance sweep technique may be employed to determine the heart rate. The minimum variance sweep technique finds the signal duration where a variance of the mean peak to peak time difference is minimum, so that the particular portion (signal duration) may contain the useful information related to the heart rate. In an embodiment, the predefined overall signal quality middle threshold value may be for example '2.3', and the predefined heart signal quality upper threshold value may be for example '2'.

In an embodiment, the heart rate is determined from the post-processed signal, using the sliding window based additive spectra technique, by further splitting the post-processed signal into one or more smaller overlapped signals, based on a predefined spectra signal window duration and a predefined signal overlap percentage value. In an embodiment, the predefined spectra signal window duration may be for example 2.5 seconds, but it should be less than that of the predefined cardiopulmonary signal window duration. In other words, the predefined cardiopulmonary signal window duration may be a multiple of the predefined spectra signal window duration. In an embodiment, each succeeding smaller overlapped signal may have the predefined signal overlap percentage value of the preceding smaller overlapped signal in the one or more smaller overlapped signals. In an embodiment, the predefined signal overlap percentage value may be 30%.

Figure 5A:
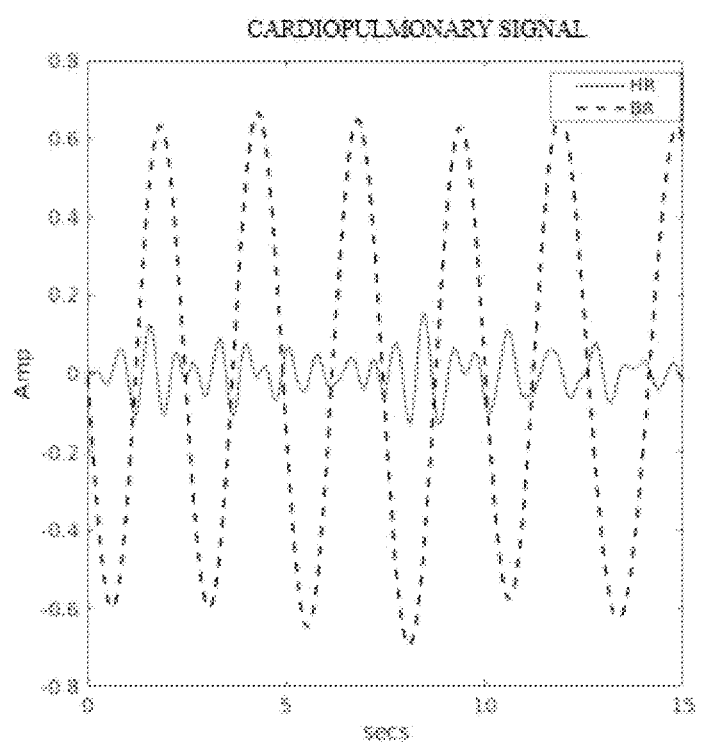
FIG. 5A and FIG. 5B illustrate graphs showing a first sample cardiopulmonary signal and an associated heart rate signal comprised in the first sample cardiopulmonary signal considered for determining the heart rate using a sliding window based additive spectra technique respectively, in accordance with some embodiments of the present disclosure.
Figure 5B:
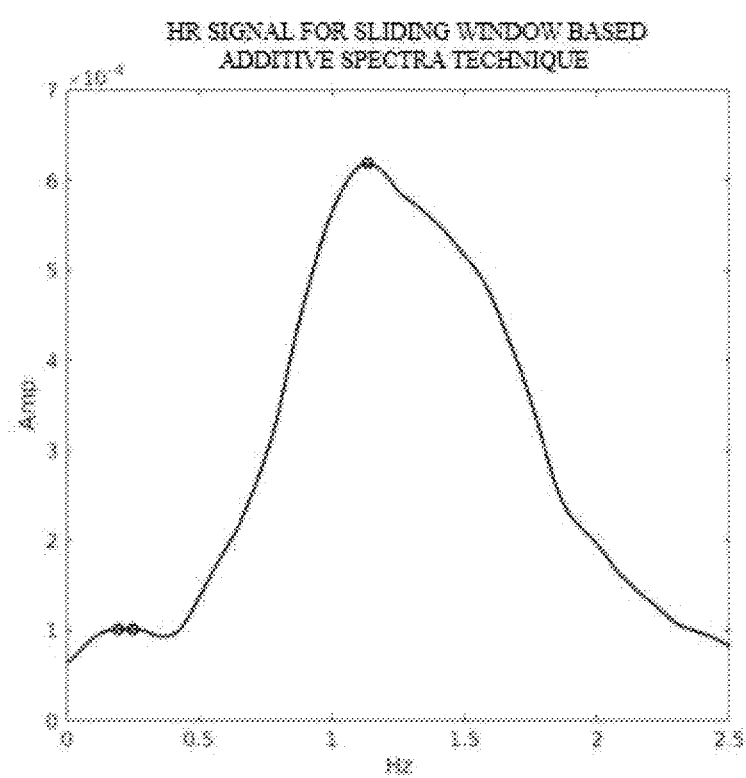

An overall frequency spectrum is generated by adding a frequency spectrum of each smaller overlapped signal of the one or more smaller overlapped signals. Breathing rate harmonics are removed from the overall frequency spectrum, based on the breathing rate obtained at step 310 of the method 300, to obtain a processed frequency spectrum. A highest peak frequency value obtained from the processed frequency spectrum gives the heart rate of the subject being monitored according to the sliding window based additive spectra technique. FIG. 5A and FIG. 5B illustrate graphs showing a first sample cardiopulmonary signal and an associated heart rate signal comprised in the first sample cardiopulmonary signal considered for determining the heart rate using a sliding window based additive spectra technique respectively, in accordance with some embodiments of the present disclosure. The associated heart rate signal comprised in the first sample cardiopulmonary signal is transformed into the frequency domain and the corresponding overall frequency spectrum is generated and the heart rate is calculated from the corresponding overall frequency spectrum. The associated heart rate signal shown in FIG. 5B contain a peak having the highest peak frequency value (showing at around 1.25 Hz) based on which the heart rate is determined.

Figure 6A:
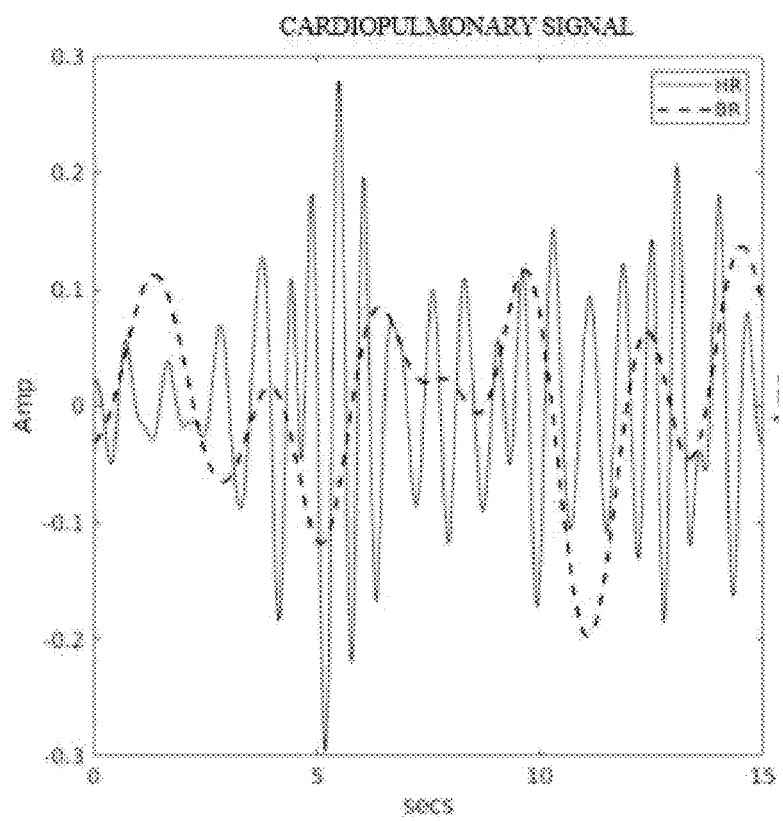
FIG. 6A and FIG. 6B illustrate graphs showing a second sample cardiopulmonary signal and the associated heart rate signal comprised in the second sample cardiopulmonary signal considered for determining the heart rate using a mean peak to peak time difference technique respectively, in accordance with some embodiments of the present disclosure.
Figure 6B:
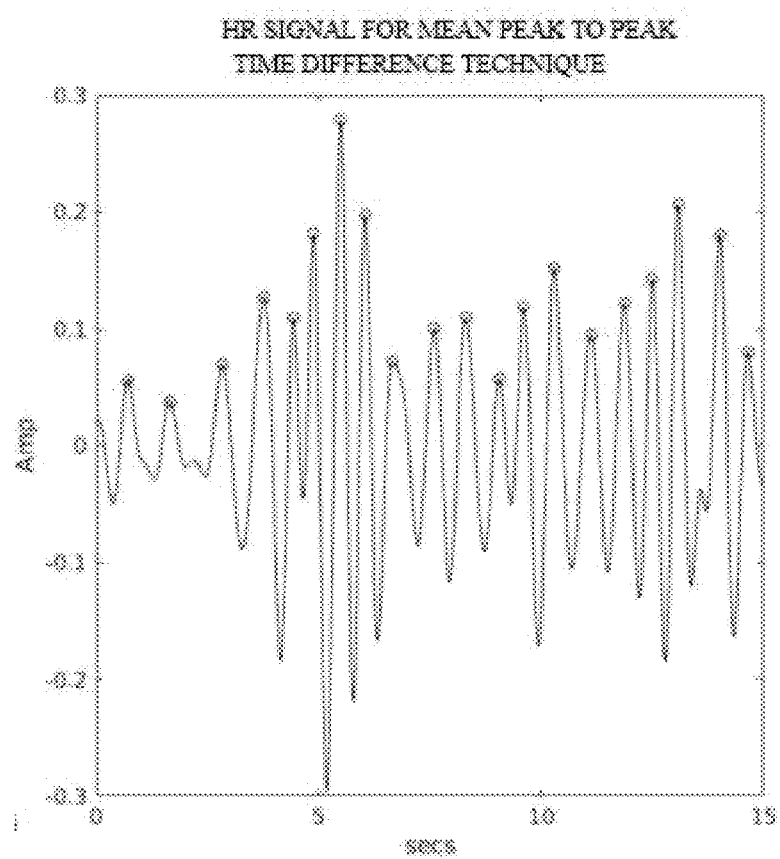

In an embodiment, the heart rate is determined from the post-processed signal, using the mean peak to peak time difference technique, by determining peak to peak time difference values, from the post-processed signal, a mean peak to peak time difference value is calculated based on the peak to peak time difference values and the heart rate of the subject being monitored is determined by inversing the mean peak to peak time difference value. FIG. 6A and FIG. 6B illustrate graphs showing a second sample cardiopulmonary signal and the associated heart rate signal comprised in the second sample cardiopulmonary signal considered for determining the heart rate using a mean peak to peak time difference technique respectively, in accordance with some embodiments of the present disclosure. The associated heart rate signal comprised in the second sample cardiopulmonary signal is utilized to determine the heart rate. The associated heart rate signal shown in FIG. 6B contain multiple peaks and the peak to peak time difference values for two consecutive peaks are calculated and then the mean peak to peak time difference value is obtained from which the heart rate is determined.

In an embodiment, the heart rate is determined from the post-processed signal, using the minimum variance sweep technique, by further splitting the post-processed signal into one or more smaller post-processed signals, based on a predefined sweep signal window duration. In an embodiment, the predefined sweep signal window duration may be for example 2.5 seconds, but it should be less than that of the predefined cardiopulmonary signal window duration. In other words, the predefined cardiopulmonary signal window duration may be a multiple of the predefined sweep signal window duration.

The peak to peak time difference values for each smaller post-processed signal of the one or more smaller post-processed signals, are determined. A peak to peak time difference variance value for each smaller post-processed signal, is calculated, based on the peak to peak time difference values present in the smaller post-processed signal. The breathing rate harmonics from the smaller post-processed signal having a minimum peak to peak time difference variance value, are removed based on the breathing rate obtained at step 310 of the method 300. A peak to peak time difference mean value is calculated, based on the peak to peak time difference values present in the smaller post-processed signal having the minimum peak to peak time difference variance value. Then the heart rate is determined by inversing the peak to peak time difference mean value.

Figure 7A:
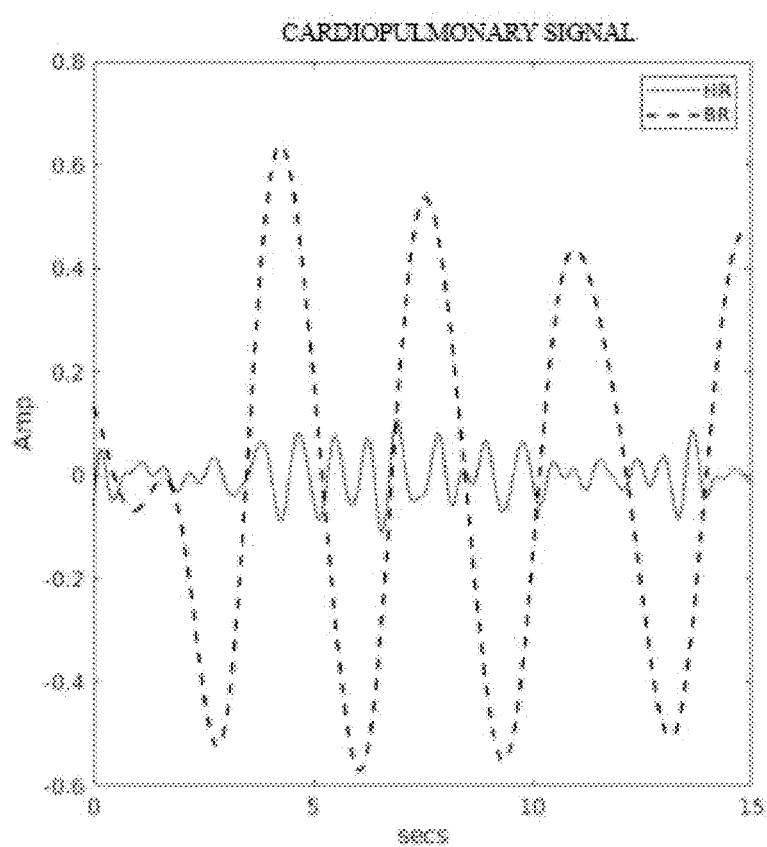
FIG. 7A and FIG. 7B illustrate graphs showing a third sample cardiopulmonary signal and the associated heart rate signal comprised in the third sample cardiopulmonary signal considered for determining the heart rate using a minimum variance sweep technique respectively, in accordance with some embodiments of the present disclosure.
Figure 7B:
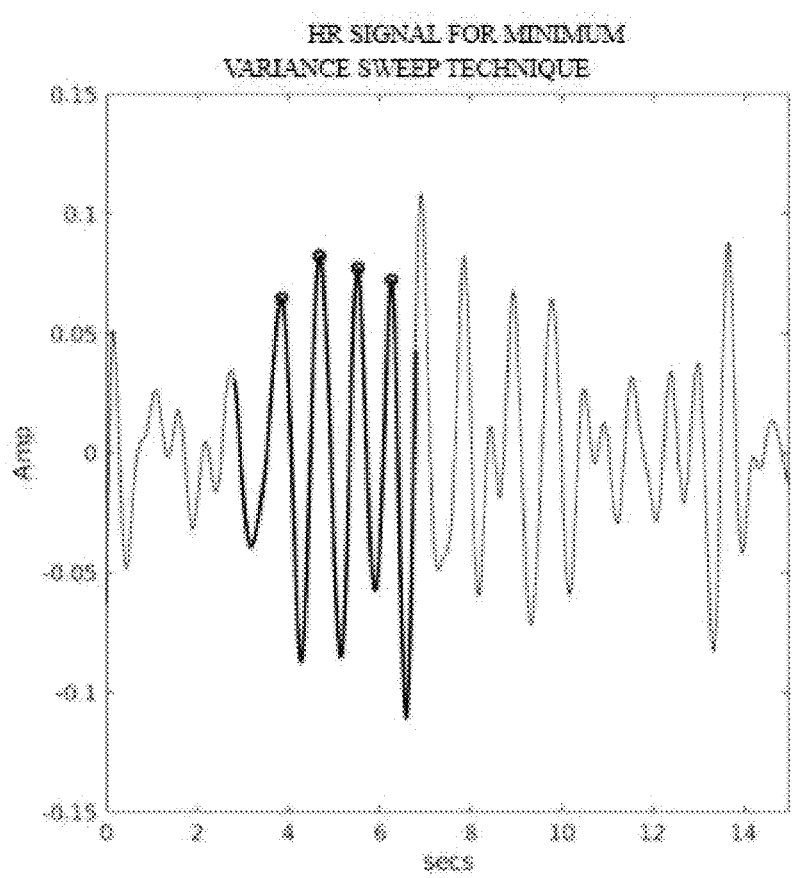

FIG. 7A and FIG. 7B illustrate graphs showing a third sample cardiopulmonary signal and the associated heart rate signal comprised in the third sample cardiopulmonary signal considered for determining the heart rate using a minimum variance sweep technique respectively, in accordance with some embodiments of the present disclosure. The associated heart rate signal comprised in the third sample cardiopulmonary signal is utilized to determine the heart rate. A portion (3 Hz to 7 Hz) having the less variance bold highlighted in associated heart rate signal shown in FIG. 7B, contain multiple peaks and the peak to peak time difference values for two consecutive peaks are calculated and then the mean peak to peak time difference value is obtained from which the heart rate is determined.

Example Scenario

Two disjoint group of subjects i.e., human beings, including 5 subjects in group 1 and 15 subjects in group 2, including both men and women in each group, aged about 25-35 years were chosen for the experiment. An indented radar system (twin radar) disclosed in the Indian patent application numbered 201921043573 of the applicant was selected as sensor unit. The twin radar has two single channel 10.525 GHz CW radars. The subjects were requested to sit on a chair at a distance of about 70 cm from the twin radar. The subjects wore normal garments (typically two layers of clothing). To minimize motion artifacts, subjects were requested to avoid sudden movements. The subjects were asked to completely relax for 5 minutes and then the cardiopulmonary signal of each subject was collected. The cardiopulmonary signal resulted from the optimal channel selection which is disclosed in the patent application numbered 201921043573 of the applicant is considered for determining the breathing rate and the heart rate in the present disclosure. For ground truth, as well as surrounding clutter information, a video recording of the subjects was done while experimentation to count the chest wall movement for calculating the breathing rate, and a pulse oximeter was used to acquire the heart rate.

Below table 1, summarizes the observations made for 2 trails for each of the 5 subjects of group 1 for determining the heart rate. The second column of the table 1 shows the accuracy of the determined heart rate with respect to the ground tooth. It is seen that the accuracy of the determined heart rate is consistently over 92% for both the trails. The second and third columns of the table 1 shows the number of peaks detected in the signal generated by the pulse oximeter and the heartbeat signal (equivalent of the post-processed signal obtained at step 312 of the method 300) respectively. The number of peaks detected through the pulse oximeter and the heartbeat signal are quite similar and corroborate with the accuracy values of determined heart rate, i.e., the accuracy is high when the number of peaks is close enough. The fourth column shows the accuracy of the heart rate variability (HRV) and we can see that the accuracy of the heart rate measurement being high implies that the parameters associated with the heart rate might have also detected precisely.

TABLE 1

| Subject No | HR Accuracy (%) | PPG data peak count | HR data peak count | HRV Accuracy (%) |
|---|---|---|---|---|
| 1.1 | 98.14 | 20 | 19 | 98.24 |
| 1.2 | 90.09 | 20 | 16 | 92.5 |

TABLE 1-continued

| Subject No | HR Accuracy (%) | PPG data peak count | HR data peak count | HRV Accuracy (%) |
|---|---|---|---|---|
| 2.1 | 98.36 | 19 | 18 | 98.85 |
| 2.2 | 93 | 17 | 19 | 95.36 |
| 3.1 | 94.29 | 21 | 19 | 95.61 |
| 3.2 | 97.32 | 21 | 20 | 96.88 |
| 4.1 | 95.99 | 20 | 21 | 94.96 |
| 4.2 | 94.76 | 20 | 22 | 93.57 |
| 5.1 | 97.03 | 18 | 19 | 97.43 |
| 5.2 | 92.11 | 19 | 23 | 94.13 |

Below table 2, summarizes the observations made for each of the 15 subjects of group 2 for determining the heart rate. It is seen that the accuracy of the determined heart rate is consistently over 92%. The number of peaks detected in the signal generated by the pulse oximeter and the heartbeat signal (equivalent of the post-processed signal obtained at step 312 of the method 300) respectively, are quite similar.

TABLE 2

| Subject No | HR Accuracy (%) | PPG data peak count | HR data peak count | HRV Accuracy (%) |
|---|---|---|---|---|
| 1 | 96.03 | 18 | 20 | 95.87 |
| 2 | 94.05 | 21 | 19 | 93.67 |
| 3 | 92.04 | 20 | 19 | 91.35 |
| 4 | 94.04 | 19 | 18 | 93.67 |
| 5 | 97.16 | 19 | 21 | 97.08 |
| 6 | 96.97 | 19 | 17 | 94.58 |
| 7 | 92.73 | 18 | 19 | 92.82 |
| 8 | 98.49 | 19 | 22 | 98.52 |
| 9 | 99.3 | 21 | 20 | 99.3 |
| 10 | 94.87 | 20 | 20 | 94.59 |
| 11 | 92.93 | 21 | 20 | 93.39 |
| 12 | 95.14 | 20 | 22 | 94.89 |
| 13 | 93.75 | 21 | 20 | 90.46 |
| 14 | 94.12 | 15 | 16 | 91.4 |
| 15 | 92.59 | 15 | 18 | 88.49 |

In accordance with the present disclosure, as seen from the experimental evaluation also, the heart rate from the cardiopulmonary signal is determined more accurately by using the best signal processing technique based on the signal quality. Hence the methods and the systems mentioned in the present disclosure can effectively detect of the vital signs including the breathing rate and the heart rate from the cardiopulmonary signals of the subject to be monitored. Hence, long-term and effective health monitoring of healthy as well as patient and infant subjects is be achieved by the present disclosure. Also, the present disclosure is sensor agnostic, since any sensor unit 110 may be used to acquire the cardiopulmonary signal from the sensor group including but are not limited to pneumotachograph, ultrasound sensors, accelerometers including wearable accelerometers, respiratory belts, and radars. The system 100 is adaptive, simple in design and flexible. Since the system 100 can be used as a portable or handheld, it can be used not only in medical care units and hospitals, but also in other areas such as fitness tracking, stress monitoring, presence detection in rescue operations and so on.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims (when included in the specification), the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for determining a breathing rate and a heart rate from cardiopulmonary signals, the method comprising the steps of:
   receiving, via one or more hardware processors, a cardiopulmonary signal of a subject being monitored from a sensor unit among a sensor group including a pneumotachograph, an ultrasound sensor, an accelerometer including a wearable accelerometer, a respiratory belt, and a radar, wherein if the sensor unit is within a system, then the system is placed beside or near to the subject being monitored to acquire the cardiopulmonary signal, wherein if the sensor unit is connected to the system but present outside the system, then the sensor unit is placed beside or near to the subject being monitored to acquire the cardiopulmonary signal of a subject wearing the sensor unit, and wherein the cardiopulmonary signal is a continuous and an unobtrusive time-domain signal represented in seconds;
   splitting, via the one or more hardware processors, the cardiopulmonary signal into one or more sub-cardiopulmonary signals, based on a predefined cardiopulmonary signal window duration, wherein the predefined cardiopulmonary signal window duration is at least 10 seconds or multiples of '5' but not '5', based on a domain knowledge;
   pre-processing, via the one or more hardware processors, each sub-cardiopulmonary signal of the one or more sub-cardiopulmonary signals, to obtain a preprocessed sub-cardiopulmonary signal, for each sub-cardiopulmonary signal;
   filtering, by a bandpass filter implemented via the one or more hardware processors connected or communicated with a portable or handheld device wirelessly or with a wired connection, through input/output (I/O) interface (s), the pre-processed sub-cardiopulmonary signal of each sub-cardiopulmonary signal, to obtain a first filtered signal and a second filtered signal, wherein the first filtered signal has frequencies between a predetermined first range of frequencies corresponding to breathing associated with the subject being monitored, and the second filtered signal has frequencies between a predetermined second range of frequencies corresponding to heartbeats associated with the subject being monitored, wherein the predetermined first range of frequencies include 0.2 Hz to 0.8 Hz, which is identified as general breathing frequency range, and wherein the predetermined second range of frequencies include 1 Hz to 2 Hz, which is identified as general heartbeats frequency range;
   determining, via the one or more hardware processors, a breathing rate of the subject being monitored, from the first filtered signal, by using a spectrum analysis technique;
   post-processing, via the one or more hardware processors, the second filtered signal to obtain a post-processed signal, wherein the post-processing comprises removing low frequency components underlying in the second filtered signal;
   obtaining, via the one or more hardware processors, an overall signal quality value of each sub-cardiopulmonary signal, and a heart signal quality value of the second filtered signal corresponding to each sub-cardiopulmonary signal, wherein obtaining the overall signal quality value of each sub-cardiopulmonary signal comprises:
      generating an overall signal autocorrelation curve whose envelope has a triangular contour, by applying an autocorrelation function on the sub-cardiopulmonary signal;
      defining an area under the envelope of the overall signal autocorrelation curve as the overall signal quality value for the sub-cardiopulmonary signal; and
   wherein obtaining the heart signal quality value of the second filtered signal corresponding to each sub-cardiopulmonary signal comprises:
      generating a heart signal autocorrelation curve whose envelope has the triangular contour, by applying the autocorrelation function on the second filtered signal corresponding to the sub-cardiopulmonary signal; and
      defining an area under the envelope of the heart signal autocorrelation curve as the heart signal quality value for the second filtered signal corresponding to the sub-cardiopulmonary signal;
   determining, via the one or more hardware processors, a heart rate of the subject being monitored, using one of a set of signal processing techniques on the post-processed signal, based on the overall signal quality value and the heart signal quality value, wherein the set of signal processing techniques comprises (i) a sliding window based additive spectra technique when (i) the overall signal quality value is greater than a predefined overall signal quality upper threshold value, and (ii) the heart signal quality value is greater than a predefined heart signal quality upper threshold value, (ii) a mean peak to peak time difference technique when (i) the overall signal quality value is greater than a predefined overall signal quality lower threshold value, or (ii) (a) the overall signal quality value is greater than a predefined overall signal quality middle threshold value and (b) the heart signal quality value is greater than a predefined heart signal quality lower threshold value, and (iii) a minimum variance sweep technique when (i) the overall signal quality value is greater than a predefined overall signal quality middle threshold value, and (ii) the heart signal quality value is greater than a predefined heart signal quality upper threshold value, wherein the minimum variance sweep technique finds a signal duration where a variance of the mean peak to peak time difference is minimum such that a particular signal duration contain useful information related to the heart rate; and,
   detecting vital signs including the breathing rate and the heart rate from the cardiopulmonary signals of the subject to be monitored, achieving long-term and effective health monitoring of healthy subjects, patients and infant subjects, and wherein the method is capable of being used in medical care units, hospitals, fitness tracking, stress monitoring, and presence detection in rescue operations.

2. The method of claim 1, wherein pre-processing each sub-cardiopulmonary signal of the one or more sub-cardiopulmonary signals, to obtain the pre-processed sub-cardiopulmonary signal, comprises:
   filtering, by the bandpass filter, each sub-cardiopulmonary signal of the one or more sub-cardiopulmonary signals, to obtain a filtered sub-cardiopulmonary signal having frequencies between a predetermined third range of frequencies corresponding to the breathing and the heartbeats associated with the subject being monitored; and
   performing, a mean removal and an amplitude normalization on the filtered sub-cardiopulmonary signal, to obtain the pre-processed sub-cardiopulmonary signal.

3. The method of claim 1, wherein the step of determining the breathing rate from the first filtered signal, using a spectrum analysis technique, comprises:
   transforming the first filtered signal to a frequency domain signal using a Fast Fourier transform (FFT) technique; and
   determining the breathing rate of the subject being monitored in breaths per minute, based on a frequency associated with a highest peak of the frequency domain signal.

4. The method of claim 1, wherein determining the heart rate from the post-processed signal, using the sliding window based additive spectra technique, comprises:
   splitting the post-processed signal into one or more smaller overlapped signals, based on a predefined spectra signal window duration and a predefined signal overlap percentage value;
   generating an overall frequency spectrum, based on a frequency spectrum of each smaller overlapped signal of the one or more smaller overlapped signals;
   removing breathing rate harmonics from the overall frequency spectrum, based on the breathing rate, to obtain a processed frequency spectrum; and
   calculating the heart rate, based on a highest peak frequency value obtained from the processed frequency spectrum.

5. The method of claim 1, wherein determining the heart rate from the post-processed signal, using the mean peak to peak time difference technique, comprises:
   determining peak to peak time difference values, from the post-processed signal;
   calculating a mean peak to peak time difference value, based on the peak to peak time difference values; and
   determining the heart rate based on the mean peak to peak time difference value.

6. The method of claim 1, wherein determining the heart rate from the post-processed signal, using the minimum variance sweep technique, comprises:
   splitting the post-processed signal into one or more smaller post-processed signals, based on a predefined sweep signal window duration;
   determining peak to peak time difference values for each smaller post-processed signal of the one or more smaller post-processed signals;
   calculating a peak to peak time difference variance value for each smaller post-processed signal, based on the peak to peak time difference values present in the smaller post-processed signal;
   removing breathing rate harmonics from the smaller post-processed signal having a minimum peak to peak time difference variance value, based on the breathing rate;
   calculating a peak to peak time difference mean value, based on the peak to peak time difference values present in the smaller post-processed signal having the minimum peak to peak time difference variance value; and
   determining the heart rate based on the peak to peak time difference mean value.

7. A system for determining a breathing rate and a heart rate from cardiopulmonary signals, the system comprising:
   a memory storing instructions; and
   one or more hardware processors coupled to the memory, wherein the one or more hardware processors are configured by the instructions to:
     receive a cardiopulmonary signal of a subject being monitored, from a sensor unit among a sensor group including a pneumotachograph, an ultrasound sensor, an accelerometer including a wearable accelerometer, a respiratory belt, and a radar, wherein if the sensor unit is within the system, then the system is configured to be placed beside or near to the subject being monitored to acquire the cardiopulmonary signal, wherein if the sensor unit is connected to the system but present outside the system, then the sensor unit is configured to be placed beside or near to the subject being monitored to acquire the cardiopulmonary signal of a subject wearing the sensor unit, and wherein the cardiopulmonary signal is a continuous and an unobtrusive time-domain signal represented in seconds;
     split the cardiopulmonary signal into one or more sub-cardiopulmonary signals, based on a predefined cardiopulmonary signal window duration, wherein the predefined cardiopulmonary signal window duration is at least 10 seconds or multiples of '5' but not '5', based on a domain knowledge;
     pre-process each sub-cardiopulmonary signal of the one or more sub-cardiopulmonary signals, to obtain a pre-processed sub-cardiopulmonary signal, for each sub-cardiopulmonary signal;
     filter, the pre-processed sub-cardiopulmonary signal of each sub-cardiopulmonary signal, to obtain a first filtered signal and a second filtered signal, using a bandpass filter connected or communicated with a portable or handheld device wirelessly or with a wired connection, through input/output (I/O) interface(s), wherein the first filtered signal having has frequencies between a predetermined first range of frequencies corresponding to breathing associated with the subject being monitored, and the second filtered signal has frequencies between a predetermined second range of frequencies corresponding to heartbeats associated with the subject being monitored, wherein the predetermined first range of frequencies include 0.2 Hz to 0.8 Hz, which is identified as general breathing frequency range, and wherein the predetermined second range of frequencies include 1 Hz to 2 Hz, which is identified as general heartbeats frequency range;
     determine a breathing rate of the subject being monitored, from the first filtered signal, by using a spectrum analysis technique;
     post-process the second filtered signal to obtain a post-processed signal, wherein the post-processing comprises removing low frequency components underlying in the second filtered signal;

obtain an overall signal quality value from each sub-cardiopulmonary signal, and a heart signal quality value from the second filtered signal corresponding to each sub-cardiopulmonary signal, wherein obtaining the overall signal quality value of each sub-cardiopulmonary signal comprises:

generating an overall signal autocorrelation curve whose envelope has a triangular contour, by applying an autocorrelation function on the sub-cardiopulmonary signal;

defining an area under the envelope of the overall signal autocorrelation curve as the overall signal quality value for the sub-cardiopulmonary signal; and wherein obtaining the heart signal quality value of the second filtered signal corresponding to each sub-cardiopulmonary signal comprises:

generating a heart signal autocorrelation curve whose envelope has the triangular contour, by applying the autocorrelation function on the second filtered signal corresponding to the sub-cardiopulmonary signal; and defining an area under the envelope of the heart signal autocorrelation curve as the heart signal quality value for the second filtered signal corresponding to the sub-cardiopulmonary signal;

determine a heart rate of the subject being monitored, using one of a set of signal processing techniques on the post-processed signal, based on the overall signal quality value and the heart signal quality value, wherein the set of signal processing techniques comprises (i) a sliding window based additive spectra technique when (i) the overall signal quality value is greater than a predefined overall signal quality upper threshold value, and (ii) the heart signal quality value is greater than a predefined heart signal quality upper threshold value, (ii) a mean peak to peak time difference technique when (i) the overall signal quality value is greater than a predefined overall signal quality lower threshold value, or (ii) (a) the overall signal quality value is greater than a predefined overall signal quality middle threshold value and (b) the heart signal quality value is greater than a predefined heart signal quality lower threshold value, and (iii) a minimum variance sweep technique when (i) the overall signal quality value is greater than a predefined overall signal quality middle threshold value, and (ii) the heart signal quality value is greater than a predefined heart signal quality upper threshold value, wherein the minimum variance sweep technique finds a signal duration where a variance of the mean peak to peak time difference is minimum such that a particular signal duration contain useful information related to the heart rate; and detect vital signs including the breathing rate and the heart rate from the cardiopulmonary signals of the subject to be monitored, achieving long-term and effective health monitoring of healthy subjects, patients and infant subjects, and wherein the system is capable of being used in medical care units, hospitals, fitness tracking, stress monitoring, and presence detection in rescue operations.

8. The system of claim 7, wherein the one or more hardware processors are further configured to pre-process each sub-cardiopulmonary signal of the one or more sub-cardiopulmonary signals, to obtain the pre-processed sub-cardiopulmonary signal, by:

filtering, by the bandpass filter, each sub-cardiopulmonary signal of the one or more sub-cardiopulmonary signals, to obtain a filtered sub-cardiopulmonary signal having frequencies between a predetermined third range of frequencies corresponding to the breathing and the heartbeats associated with the subject being monitored; and performing, a mean removal and an amplitude normalization on the filtered sub-cardiopulmonary signal, to obtain the pre-processed sub-cardiopulmonary signal.

9. The system of claim 7, wherein the one or more hardware processors are further configured to determine the breathing rate from the first filtered signal, using a spectrum analysis technique, by:

transforming the first filtered signal to a frequency domain signal using a Fast Fourier transform (FFT) technique; and determining the breathing rate of the subject being monitored in breaths per minute, based on a frequency associated with a highest peak of the frequency domain signal.

10. The system of claim 7, wherein the one or more hardware processors are further configured to determine the heart rate from the post-processed signal, using the sliding window based additive spectra technique, by:

splitting the post-processed signal into one or more smaller overlapped signals, based on a predefined spectra signal window duration and a predefined signal overlap percentage value;

generating an overall frequency spectrum, based on a frequency spectrum of each smaller overlapped signal of the one or more smaller overlapped signals;

removing breathing rate harmonics from the overall frequency spectrum, based on the breathing rate, to obtain a processed frequency spectrum; and calculating the heart rate, based on a highest peak frequency value obtained from the processed frequency spectrum.

11. The system of claim 7, wherein the one or more hardware processors are further configured to determine the heart rate from the post-processed signal, using the mean peak to peak time difference technique, by:

determining peak to peak time difference values, from the post-processed signal; calculating a mean peak to peak time difference value, based on the peak to peak time difference values; and determining the heart rate based on the mean peak to peak time difference value.

12. The system of claim 7, wherein the one or more hardware processors are further configured to determine the heart rate from the post-processed signal, using the minimum variance sweep technique, by:

splitting the post-processed signal into one or more smaller post-processed signals, based on a predefined sweep signal window duration;

determining peak to peak time difference values for each smaller post-processed signal of the one or more smaller post-processed signals;

calculating a peak to peak time difference variance value for each smaller post-processed signal, based on the peak to peak time difference values present in the smaller post-processed signal;

removing breathing rate harmonics from the smaller post-processed signal having a minimum peak to peak time difference variance value, based on the breathing rate;

calculating a peak to peak time difference mean value, based on the peak to peak time difference values present in the smaller post-processed signal having the minimum peak to peak time difference variance value; and determining the heart rate based on the peak to peak time difference mean value.

13. A computer program product comprising a non-transitory computer readable medium having a computer readable program embodied therein, wherein the computer readable program, when executed on a computing device, causes the computing device to:

receive a cardiopulmonary signal of a subject being monitored, from a sensor unit among a sensor group including a pneumotachograph, an ultrasound sensor, an accelerometer including a wearable accelerometer, a respiratory belt, and a radar, wherein if the sensor unit is within a system, then the system is configured to be placed beside or near to the subject being monitored to acquire the cardiopulmonary signal, wherein if the sensor unit is connected to the system but present outside the system, then the sensor unit is configured to be placed beside or near to the subject being monitored to acquire the cardiopulmonary signal of a subject wearing the sensor unit, and wherein the cardiopulmonary signal is a continuous and an unobtrusive time-domain signal represented in seconds;

split the cardiopulmonary signal into one or more sub-cardiopulmonary signals, based on a predefined cardiopulmonary signal window duration, wherein the predefined cardiopulmonary signal window duration is at least 10 seconds or multiples of '5' but not '5', based on a domain knowledge;

pre-process each sub-cardiopulmonary signal of the one or more sub-cardiopulmonary signals, to obtain a pre-processed sub-cardiopulmonary signal, for each sub-cardiopulmonary signal;

filter, the pre-processed sub-cardiopulmonary signal of each sub-cardiopulmonary signal, to obtain a first filtered signal and a second filtered signal, using a band-pass filter connected or communicated with a portable or handheld device wirelessly or with a wired connection, through input/output (I/O) interface(s), wherein the first filtered signal has frequencies between a predetermined first range of frequencies corresponding to breathing associated with the subject being monitored, and the second filtered signal has frequencies between a predetermined second range of frequencies corresponding to heartbeats associated with the subject being monitored, wherein the predetermined first range of frequencies include 0.2 Hz to 0.8 Hz, which is identified as general breathing frequency range, and wherein the predetermined second range of frequencies include 1 Hz to 2 Hz, which is identified as general heartbeats frequency range;

determine a breathing rate of the subject being monitored, from the first filtered signal, by using a spectrum analysis technique; post-process the second filtered signal to obtain a post-processed signal, wherein the post-processing comprises removing low frequency components underlying in the second filtered signal;

obtain an overall signal quality value from each sub-cardiopulmonary signal, and a heart signal quality value from the second filtered signal corresponding to each sub-cardiopulmonary signal, wherein obtaining the overall signal quality value of each sub-cardiopulmonary signal comprises:

generating an overall signal autocorrelation curve whose envelope has a triangular contour, by applying an autocorrelation function on the sub-cardiopulmonary signal;

defining an area under the envelope of the overall signal autocorrelation curve as the overall signal quality value for the sub-cardiopulmonary signal; and wherein obtaining the heart signal quality value of the second filtered signal corresponding to each sub-cardiopulmonary signal comprises:

generating a heart signal autocorrelation curve whose envelope has the triangular contour, by applying the autocorrelation function on the second filtered signal corresponding to the sub-cardiopulmonary signal; and defining an area under the envelope of the heart signal autocorrelation curve as the heart signal quality value for the second filtered signal corresponding to the sub-cardiopulmonary signal;

determine a heart rate of the subject being monitored, using one of a set of signal processing techniques on the post-processed signal, based on the overall signal quality value and the heart signal quality value, wherein the set of signal processing techniques comprises (i) a sliding window based additive spectra technique when (i) the overall signal quality value is greater than a predefined overall signal quality upper threshold value, and (ii) the heart signal quality value is greater than a predefined heart signal quality upper threshold value, (ii) a mean peak to peak time difference technique when (i) the overall signal quality value is greater than a predefined overall signal quality lower threshold value, or (ii) (a) the overall signal quality value is greater than a predefined overall signal quality middle threshold value and (b) the heart signal quality value is greater than a predefined heart signal quality lower threshold value, and (iii) a minimum variance sweep technique when (i) the overall signal quality value is greater than a predefined overall signal quality middle threshold value, and (ii) the heart signal quality value is greater than a predefined heart signal quality upper threshold value, wherein the minimum variance sweep technique finds a signal duration where a variance of the mean peak to peak time difference is minimum such that a particular signal duration contain useful information related to the heart rate; and detect vital signs including the breathing rate and the heart rate from the cardiopulmonary signals of the subject to be monitored, achieving long-term and effective health monitoring of healthy subjects, patients and infant subjects, and wherein the computer program product is capable of being used in medical care units, hospitals, fitness tracking, stress monitoring, and presence detection in rescue operations.

\* \* \* \* \*